US011505823B2

(12) United States Patent
Bordy et al.

(10) Patent No.: US 11,505,823 B2
(45) Date of Patent: *Nov. 22, 2022

(54) MICROFLUIDIC DEVICE INCLUDING AN AMPLIFICATION REACTION CHAMBER

(71) Applicant: Commissariat a l'Energie Atomique et aux Energies Alternatives, Paris (FR)

(72) Inventors: Thomas Bordy, Grenoble (FR); Anne-Gaelle Bourdat, Grenoble (FR); Remi Toutain, Grenoble (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 13 days.

This patent is subject to a terminal disclaimer.

(21) Appl. No.: 16/930,765

(22) Filed: Jul. 16, 2020

(65) Prior Publication Data
US 2021/0017573 A1    Jan. 21, 2021

(30) Foreign Application Priority Data
Jul. 17, 2019   (FR) ...................... 19 08033

(51) Int. Cl.
*C12Q 1/686*    (2018.01)
*B01L 3/00*    (2006.01)
*B01L 9/00*    (2006.01)

(52) U.S. Cl.
CPC ........ *C12Q 1/686* (2013.01); *B01L 3/502715* (2013.01); *B01L 9/527* (2013.01); *B01L 2200/027* (2013.01); *B01L 2300/0627* (2013.01)

(58) Field of Classification Search
CPC ............ C12Q 2545/101; C12Q 1/6844; C12Q 2565/629; C12Q 1/686; B01L 2200/027;
(Continued)

(56) References Cited

U.S. PATENT DOCUMENTS

2010/0009431 A1    1/2010   Cho et al.
2017/0113221 A1*   4/2017   Hoffman ................. B01L 3/527
(Continued)

FOREIGN PATENT DOCUMENTS

EP    3 173 469 A1    5/2017
EP    3 222 989 A1    9/2017
JP    2009-098039 A   5/2009

OTHER PUBLICATIONS

French Preliminary Search Report dated Dec. 17, 2019 in French Application 19 08033 filed on Jul. 17, 2019 (with English Translation of Categories of Cited Documents & Written Opinion), 11 pages.

*Primary Examiner* — Young J Kim
(74) *Attorney, Agent, or Firm* — Oblon, McClelland, Maier & Neustadt, L.L.P.

(57) ABSTRACT

A microfluidic system is intended for the analysis of a biological sample containing biological species. The system includes an optical detection device having a source configured to emit an optical signal and at least one sensor having a capture surface defining an optical signal reading zone. The system also includes a microfluidic device having a support in which an amplification chamber, in which an amplification reaction can be carried out, is made, and having an input channel opening into the amplification chamber. The amplification chamber includes at least one first zone located in the sensor reading zone and at least one protuberance forming a recess intended to receive a compound for internal control of the amplification reaction and arranged to be located outside the sensor reading zone or configured to be opaque to said optical signal.

8 Claims, 4 Drawing Sheets

(58) Field of Classification Search
CPC ....... B01L 2200/143; B01L 2300/0627; B01L 3/502715; B01L 7/52; B01L 9/527
See application file for complete search history.

(56) References Cited

U.S. PATENT DOCUMENTS

| | | |
|---|---|---|
| 2017/0151571 A1 | 6/2017 | Kim et al. |
| 2017/0268041 A1 | 9/2017 | Gosselin et al. |
| 2021/0016282 A1* | 1/2021 | Bordy ............... B01L 3/502715 |

* cited by examiner

MICROFLUIDIC DEVICE INCLUDING AN AMPLIFICATION REACTION CHAMBER

TECHNICAL FIELD OF THE INVENTION

The present invention relates to a microfluidic system, more particularly to the architecture of a chamber located in a device of the system and intended for the implementation of an amplification reaction.

RELATED ART

The qPCR reaction consists of amplification of a targeted DNA or RNA sequence (representative of a particular organism) coupled to an intercalator or a probe producing a fluorescence that can be detected by an optical apparatus if this sequence is amplified. Thus, an increase in fluorescence means that the amplification reaction is taking place and that the DNA or RNA of the target organism was in fact present. If there is no reaction, however, it must be clear that this is due to the absence of the target organism and not to the inhibition of the amplification reaction, which would result in a false negative. The enzymes responsible for the amplification reaction are indeed sensitive to many inhibitors provided by the sample being tested.

To ensure that the absence of amplification means the absence of the target, internal reaction controls are used. These are most often another DNA target added intentionally to the test that will be amplified simultaneously with the sample of interest. It is then necessary to be able to discriminate between the two reactions. Several strategies are used in the industry:

- One could be to use part of the sample to carry out the control in parallel, as an independent reaction. This requires splitting the initial sample, resulting in a loss of sensitivity/representativeness of the test. The advantage is that it is possible to use any amplification detection technique for this control (fluorescent DNA intercalation, for example).
- In order not to split the sample, another strategy consists in performing the control in the same reaction as the target sequence. This solution allows testing of the entire sample but is not compatible with all detection techniques, notably with the use of non-specific intercalating agent, a sequence or any other non-sequence-specific detection mode (colorimetry, pH-metry . . . ).

Patent application EP0586112A2 and U.S. Pat. No. U.S. Pat. No. 6,312,930B1 each describe a detection method for eliminating false negatives, by adding a control target.

The invention therefore aims to provide a microfluidic system equipped with an integrated solution to control the amplification reaction or to identify several targets during the same analysis.

DISCLOSURE OF THE INVENTION

This aim is achieved by a microfluidic system intended for the analysis of a biological sample containing biological species, said system comprising:

- An optical detection device comprising a source configured to emit an optical signal and at least one sensor having a capture surface defining an optical signal reading zone,
- A microfluidic device which comprises:
  - A support in which a so-called amplification chamber, in which an amplification reaction can be carried out, is made,
  - An input channel opening into said amplification chamber,
  - The amplification chamber comprising at least one first zone located in the sensor reading zone and at least one protuberance forming a recess intended to receive a compound for internal control of the amplification reaction and arranged to be located outside the sensor reading zone or configured to be opaque to said optical signal.

According to one feature, the amplification chamber comprises a first volume having a first section and a second volume having a second section narrowed with respect to said first section so as to form a protuberance, said protuberance forming said recess.

According to another feature, said support comprises several superimposed strata and said amplification chamber is made by at least two of said superimposed strata, called upper stratum and lower stratum, said recess is made in only one of said two strata.

According to another feature, said protuberance forming said recess is made in the lower stratum.

According to another feature, the amplification chamber comprises a main cavity made in the upper stratum and one or more secondary cavities made in the lower stratum and each forming another recess of said chamber.

According to another feature, the internal reaction control compound contains a known DNA sequence or set of DNA primers targeting a predefined DNA target, allowing its amplification according to the amplification method used.

According to another feature, the first zone of the chamber is transparent to allow an optical signal supplied by a source of the detection device to pass through and the second zone has at least one opaque portion configured not to allow said optical signal to pass through.

The invention also relates to a method for analyzing a biological sample containing biological species, said method being implemented by a system as defined above and consisting in:

- Placing an internal reaction control compound in the recess of the amplification chamber,
- Injecting a fluidic sample into the amplification chamber of the microfluidic device,
- Detecting with the sensor the presence of a target compound contained in said fluidic sample and located in the first zone of the amplification chamber,
- Detecting, with a time lag, the presence of the internal reaction control compound in the first zone of the amplification chamber.

BRIEF DESCRIPTION OF THE FIGURES

Other features and advantages will become apparent in the following detailed description which refers to the appended drawings, wherein.

DETAILED DESCRIPTION OF AT LEAST ONE EMBODIMENT

The microfluidic device of the invention is intended for the analysis of a biological sample. This biological sample is for example in the form of a fluid which contains biological species containing biological material to be studied.

Biological species means notably microorganisms, cells, spores, viruses. . . . Biological material to be studied means, for example, nucleic acid molecules (RNA, DNA) derived from a cell, proteins, lipopolysaccharides (LPS), lipoteichoic acids (LTA) . . . .

Fluid means a liquid, a gas. . . . The liquid may have different degrees of viscosity and may for example be in paste or gel form.

In the remainder of the description, the terms "lower", "upper", "top" and "bottom" used are to be understood with reference to a main axis (X) which is vertical.

In the remainder of the description, the terms "external", "outside", "internal", "inside" should be understood by reference to the chambers of the device which will be described below.

Figure 1:
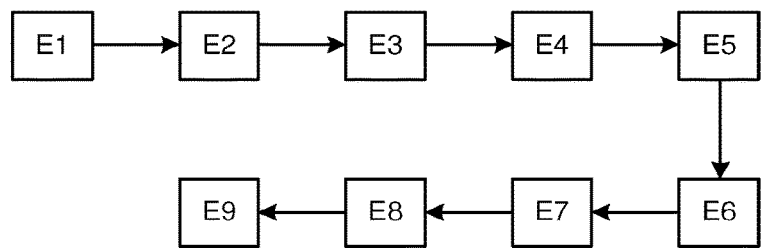
FIG. 1 is a diagram showing all the steps of a method for the preparation and analysis of a biological sample by biomolecular amplification.

With reference to FIG. 1, the complete analysis of a biological sample as defined above may involve the following steps carried out in sequence:
  E1: Concentration of biological species present in the biological sample,
  E2: Washing for purification, to remove culture interferents,
  E3: Provision of a culture medium,
  E4: Culture of biological species,
  E5: Optical growth monitoring during culture and colony counting,
  E6: Washing, to remove PCR inhibitors,
  E7: Mechanical lysis of the biological species present in the sample in order to extract biological material to be studied,
  E8: Separation between the biological material to be studied and the pollutants present, and
  E9: Detection of the presence of pathogens in the biological material by qPCR, LAMP, RPA type biomolecular amplification and optical detection such as fluorescence, colorimetry, holographic imaging, turbidimetry, pH-metry in connection with the amplification reaction.

Of course, not all of these steps are necessarily performed in the device, as the method may be limited to only certain steps.

In the concentration step, the biological sample, for example in liquid form, including the biological species, is injected into a chamber to pass through a filter. The liquid portion of the sample and any particles/molecules passing through the filter are collected through a discharge channel and discarded from the analysis. The biological species are then concentrated in a space in the chamber.

A wash/rinse solution can be injected to wash the biological species present in the chamber.

A culture medium is injected to allow the culture of biological species.

The growth monitoring step allows, by optical reading, using a sensor C, cell growth to be monitored during the culture step.

Mechanical lysis of biological species is used to grind the biological species present in the sample against a rough bearing surface. Once mechanical lysis has been carried out, a biological material, formed for example of DNA molecules and pollutants, is available for study.

Separation between the biological material to be studied and the pollutants is achieved by injecting a liquid solution containing amplification reagents to elute the biological material to be studied. Part of the injected liquid solution thus carries away the biological material to be studied, for example DNA molecules, which passes through the filter.

Once the separation between the pollutants and the biological material to be studied is completed, the biological material amplification reaction detects the presence of a pathogen in the separated biological material. The amplification reaction is carried out by adding an amplification mixture and heating a chamber in which the sample is placed. The temperature to which the chamber is heated depends on the type of amplification reaction performed. This can be any type of amplification reaction, for example loop-mediated isothermal amplification (LAMP), polymerase chain reaction (PCR), nucleic acid sequence-based amplification (NASBA), recombinase polymerase amplification (RPA). . . . For LAMP, heating is carried out at a temperature advantageously comprised between 60° C. and 65° C. This reaction makes it possible to amplify the molecules of the biological material to be detected, for example DNA molecules. During the biological material amplification reaction, the aim is to detect whether a pathogen is present. Different methods can be used for this, such as for example colorimetry, fluorescence, electrochemistry, pH-metry, turbidimetry. Any other detection method could be considered. For a detection method such as PH-metry, pH detection electrodes could be integrated into the device.

Figure 2:
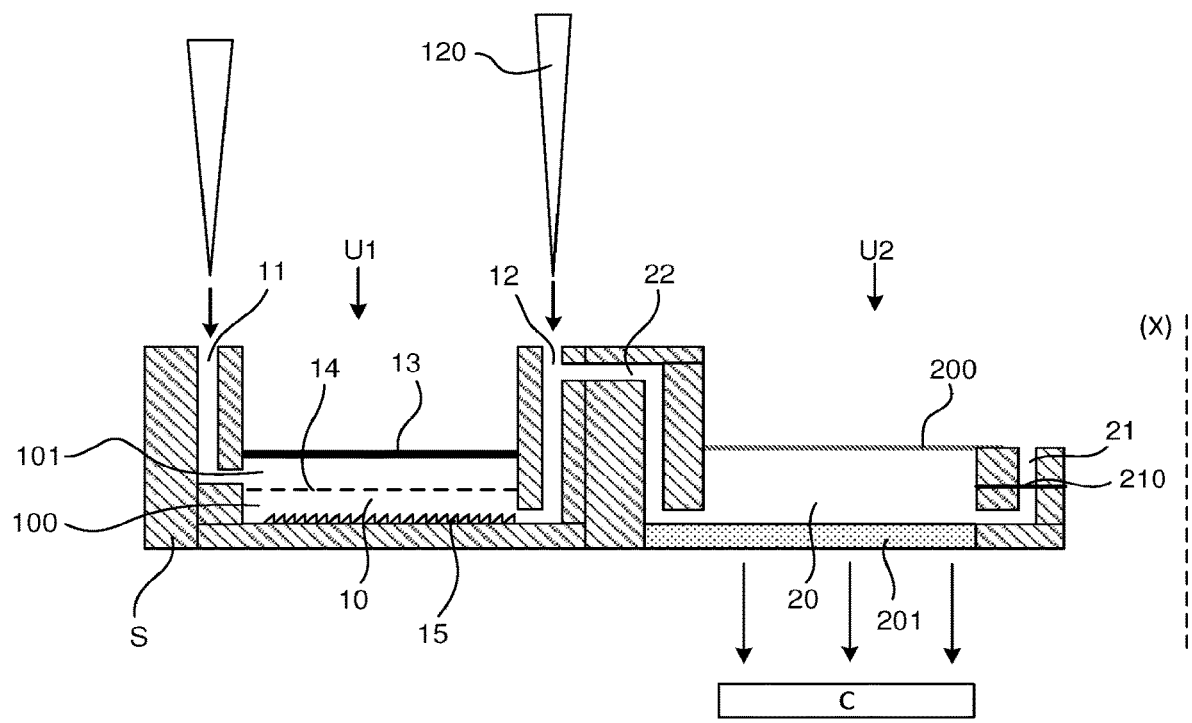
FIG. 2 shows a two-unit microfluidic device for carrying out the steps of the preparation and analysis method defined in FIG. 1.
Figure 3:
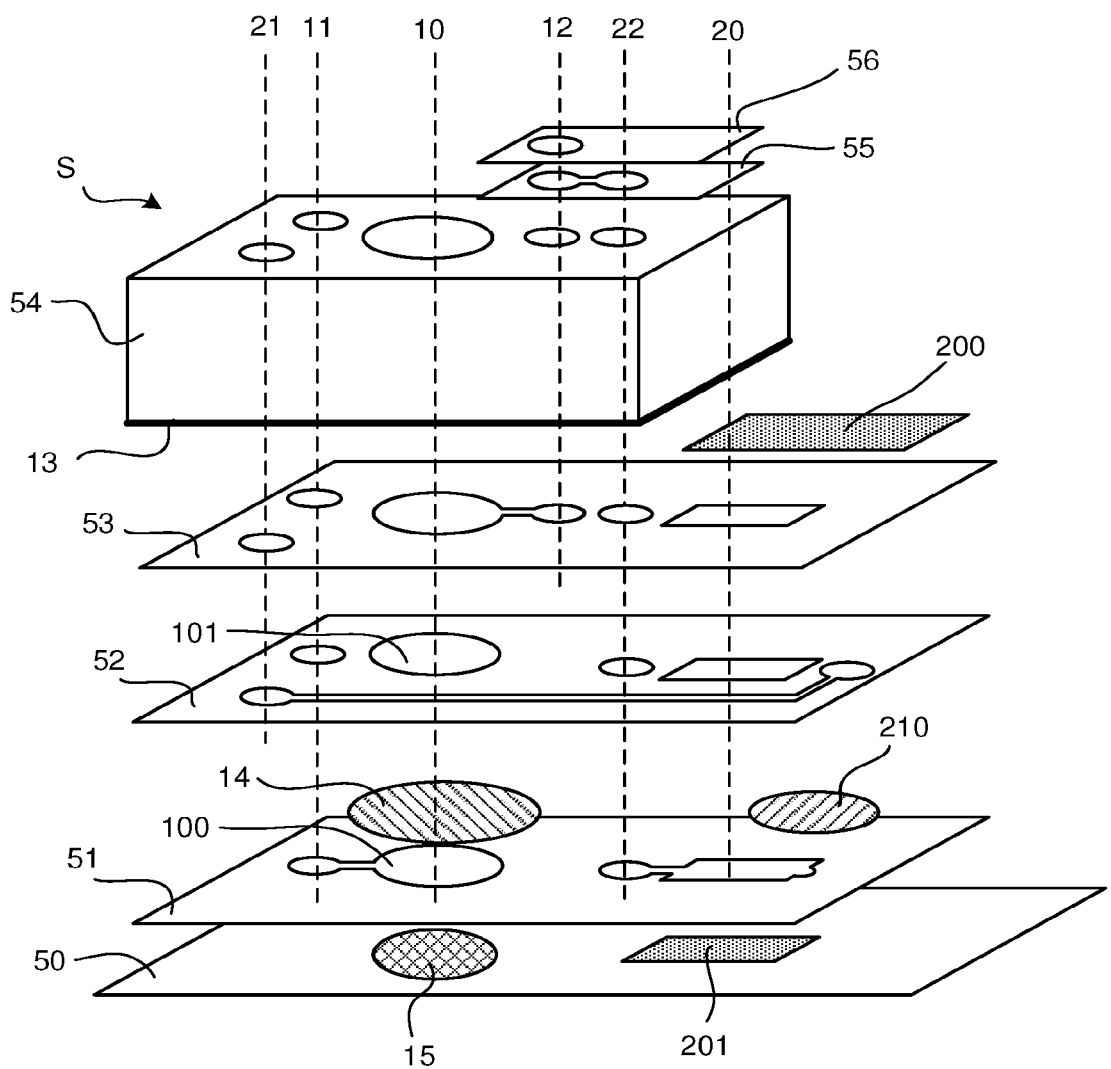
FIG. 3 shows an example of the embodiment of the device of FIG. 2, in exploded view.

A microfluidic device for performing the above steps is shown in FIG. 2. This device consists of a single rigid support S. FIG. 3 described below gives an example of an embodiment of the device.

This rigid support S integrates a microfluidic network adapted to the implementation of the steps of the analysis method. It will be seen that the microfluidic network can take different architectures according to the configuration of the analysis method that is implemented.

The support S advantageously comprises a flat bottom wall and a multilayer architecture stacked along said main axis on its bottom wall.

The microfluidic network of the device consists of at least two units U1, U2.

The first unit U1 has a first chamber 10 made in said support. This chamber 10 has a non-zero volume and is delimited by walls of the support S.

The first unit U1 has a first channel 11 made in the support for injecting fluids into or discharging fluids from the first chamber 10. The first channel 11 has a first end with an opening formed for example through a top wall of the support S and a second end which opens into said first chamber 10. The first end of the first channel is for example arranged vertically and its second end opens, for example horizontally, into the first chamber 10.

The first unit U1 has a second channel 12. This second channel 12 also has a first end which communicates with the outside, forming an opening made for example through a top wall of the support S and a second end which communicates with the space formed by the first chamber 10. Through this second channel 12, fluids can also be injected into said first chamber or discharged from said first chamber. Its first end is for example arranged vertically and its second end horizontally. The first chamber 10 is located between the first channel 11 and the second channel 12.

Towards the top, the first chamber 10 can be closed by a flexible and stretchable membrane 13. At the level of the first chamber, a top wall of the support thus has an opening which is covered in a sealed manner by said membrane 13. The membrane 13 is thus anchored in the support by means of any suitable fastening solution, for example by gluing. This membrane 13 will for example be composed of a film, for example of type MicroAmp, 3M (registered trademarks), of thickness, dimensions and constitution adapted to deform hyperelastically with respect to its anchoring points, at least to the bottom of the first chamber.

The membrane 13 is able to deform reversibly between several configurations. It can be stretched by hyperelastic deformation towards the outside of the support S, retract inside the first chamber 10 by compression, or be at rest. Hyperelastic material means a material capable of having a surface that can pass from a first surface area to a second surface area, the second surface area being equal to at least 5 times the first surface area, for example 10 times or even 50 times the first surface area.

The first unit U1 also comprises a transverse filter 14 arranged in said first chamber 10 and separating said first chamber 10 into two spaces 100, 101. The two spaces are for example superimposed and thus designated as a lower space 100 located below the filter 14 and an upper space 101 located above the filter 14. This filter 14 is preferably made in whole or in part in the form of a thin flexible film, drawn into the space formed by the chamber so as to allow passage from one space to the other only through the pores of the filter 14. The film has an elastic deformability enabling it to stretch when a bearing force is exerted in a substantially vertical direction, this elastic deformability having a level sufficient to reach the bottom of the chamber 10. The filter 14 has an average pore diameter comprised between 0.2 µm and 50 µm, for example comprised between 0.2 µm and 1 µm for the separation of microorganisms. The pore diameter is of course adapted to ensure separation between different biological species present in the sample. The filter 14 will be for example composed of a film of suitable thickness, dimensions and constitution to deform to the bottom of the chamber 10 in relation to its anchorage points. It may have the same characteristics of hyperelasticity as the membrane.

According to one feature, the first channel 11 opens into the upper space 101 of the first chamber 10 and the second channel 12 opens into the lower space 100 of the first chamber 10. The mouths of the two channels are therefore separated by the filter 14 arranged in the chamber.

With reference to FIG. 2, the first unit U1 can advantageously have a rough bearing surface 15 arranged on the bottom of the first chamber 10. This rough bearing surface 15 extends over a majority of the bottom of the first chamber. It has an average surface roughness parameter comprised between 0.1 µm and 10 µm, preferentially comprised between 0.2 µm and 3 µm. This rough bearing surface 15 is intended to allow mechanical lysis of the biological species present in a biological sample placed in the device. Preferentially, the mechanical lysis is carried out by grinding said biological species by abrasion on said rough support surface. The grinding operation is carried out by a frictional movement of the biological species against the rough bearing surface, using a suitable grinding member. This grinding device may be a spatula or a rod, for example made of plastic or metal. This grinding element is applied from outside chamber 10 and its end is pressed against the outer surface of the membrane 13 so as to stretch the membrane 13 and the filter 14 towards the bottom of the first chamber 10 and thus rub the biological species present in a sample against the roughened bearing surface 15.

For its part, the second unit U2 of the device comprises a second chamber 20 of non-zero volume, delimited by walls of the support S. The second unit U2 also comprises a third channel 21 formed in said support. This third channel 21 comprises a first end comprising an opening formed for example through an upper wall of the support and a second end which opens only into said second chamber 20. The first end of this third channel 21 is for example arranged vertically and its second end opens for example horizontally into the second chamber 20. The first end of this third channel is for example sealed by a hydrophobic membrane 210, i.e. which is impermeable to liquid but permeable to gas such as air. This hydrophobic membrane 210 can be made of a polytetrafluoroethylene (PTFE) type material.

Two transverse walls of the support, advantageously a parallel upper wall 200 and lower wall 201, partially delimiting the second chamber 20, are made of a transparent material, thus allowing an optical reading through the volume of the second chamber. The term "transparent" means that the material used is at least partially transparent to visible light, so as to allow at least 80% of this light to pass through. This means that it will be sufficiently transparent to see the inside of the chamber. The lower wall may be made of glass and the upper wall may be made of a removable adhesive bonded to close the second chamber on the upper side.

According to one feature of the invention, the device also comprises a first transfer channel 22 made in said support. This first transfer channel 22 is intended to connect the first chamber 10, more precisely its lower space 100, to the second chamber 20.

Advantageously, the first transfer channel 22 has a first end opening directly into the second channel 12, thus forming a bypass node on this second channel 12. It has a second end opening directly into the second chamber.

The device further comprises switching means which can be for example arranged on the second channel 12 to select the connection of the first chamber:

To the outside only via the second channel only or,
To the second chamber only through the first transfer channel.

These switching means may consist of a hollow removable cone 120 in the form of a funnel. When it is inserted by its tip into the second channel 12, it allows communication between the outside and the first chamber and its wall closes off the entrance to the first transfer channel 22, made at the bypass node. When it is removed, the first end of the second channel 12 can be closed off, for example with an adhesive 121 applied to a surface of the support, and the connection between the first transfer channel 22 and the second channel 12 is then opened, allowing a fluid to flow between the first chamber 10 and the second chamber 20.

Of course, the switching means can also be made in other alternative embodiments. The general principle being to be able to access the first chamber by closing the transfer channel or to allow a connection between the first chamber and the second chamber. It can thus be a simple valve which:

In a first position, allows access to the second channel by blocking the mouth of the transfer channel 22 at the bypass node,
In a second position, opens the connection between the second channel 12 and the transfer channel 22.

Without limitation, the device can be made according to the architecture shown in FIG. 3.

In this FIG. 3, the support S has the following features:
The support has a slide 50, for example made of glass or of PMMA or COC type plastic;
The slide 50 is covered in a first zone with an abrasive surface so as to form on a part of its upper side the rough bearing surface 15 dedicated to lysis;
In at least one second zone the slide 50 is transparent to form the transparent bottom wall 201 of the second chamber 20 for optical reading;
A first layer 51 bearing a first microfluidic imprint is deposited on the upper face of the slide 50, this first imprint comprising a first cavity defining the lower space 100 of the first chamber 10, a second cavity defining a lower part of the second chamber 20 and the lower part of the third channel 21; the first cavity has its edges arranged around the first abrasive zone and the second cavity has its edges arranged around the second reading zone;
The filter 14 is applied to the first layer to cover the lower space 100 of the first chamber and the hydrophobic membrane 210 is applied to the lower part of the third channel 21;
A second layer 52 bearing a second microfluidic imprint is deposited on top of the first layer 51, also covering the filter 14 and the hydrophobic membrane 210. This second microfluidic imprint comprises a cavity forming the upper space 101 of the first chamber 10, a second cavity forming a middle part of the second chamber 20 and the upper part of the third channel 21;
A third layer 53 bearing a third microfluidic imprint is deposited on the upper side of the second layer 52; this third microfluidic imprint comprises the upper part of the first chamber 10 and the upper part of the second chamber 20;
A glass or plastic strip is dimensioned to cover the upper side of the third layer 53 at the second chamber, forming the upper transparent wall 200 of the carrier;
A cap 54, for example made of PMMA, is positioned above the first chamber 10; on its underside, the cap has the membrane 13 intended to close the first chamber from above;
The cover has an upper axial opening, allowing access to the membrane 13, for lysis;
The cap 54 has two fluid inlets/outlets on its upper side. The first inlet/outlet is connected to a first axial through-channel formed through the membrane 13 and the three layers and opening into the first chamber 10 to form the first channel 11 of the support; the second inlet/outlet is connected to a second axial through-channel formed through the membrane 13 and the second and third layers and opening above the hydrophobic membrane 210, to form the third channel 21 of the support;
Finally, the support has two other through channels forming the first transfer channel 22 connecting the two chambers 10, 20;
Two other layers 55, 56 allow the input of the second channel 12 and the junction of the transfer channel 22 on this second channel 12;

The invention relates more particularly to the second chamber 20, known as the amplification chamber. This amplification chamber has an architecture adapted to the implementation of the detection step described above.

The amplification chamber has an appropriately shaped internal volume, either to ensure reliable control of the amplification reaction or to identify several targets simultaneously. In the latter case, the chamber can be shaped to allow multiple targets to be identified simultaneously. These tests, known as multiplex tests, are for example used to detect groups of pathogenic organisms corresponding to similar clinical symptoms or to detect a bacterium but also its potential antibiotic resistance genes.

The principle is to create at least one recess Ax (x ranging from 1 to N, N corresponding to the number of recesses and being greater than or equal to 1) in the amplification chamber, to house an internal reaction control compound (for example a selected DNA sequence or amplification primers targeting a predefined DNA) adapted to the amplification technology used (PCR, LAMP RPA . . . ). According to this principle, either the DNA is dried in the recess, the primers are then brought by the liquid introduced into the chamber, or the primers are dried in the recess and the DNA is brought by the liquid introduced into the chamber.

This recess Ax is advantageously created outside the section of the chamber dedicated to optical reading. The section of the chamber dedicated to optical reading corresponds to an optical reading zone Z. The optical reading zone Z is the only zone of the chamber visible by a sensor C. The chamber may have zones outside this optical reading zone Z, and therefore outside the reading field of the sensor C.

In the case of reaction control, the internal control compound can be deposited in the recess Ax at a known concentration and then dried directly in the chamber. It thus remains permanently in the device and is ready for use.

The advantage of depositing the compound not directly in the optical reading zone Z but outside it makes it possible, in addition to optimizing the gas exchange space, to differentiate the control amplification from the target amplification. The control amplification will indeed be both temporally and spatially shifted.

The architecture of the multilayer device allows the amplification chamber to be built with strata of different designs. The lower stratum may indeed have one or more recesses and the upper strata of the chamber define the total optical reading cross section of the chamber.

Figure 4A:
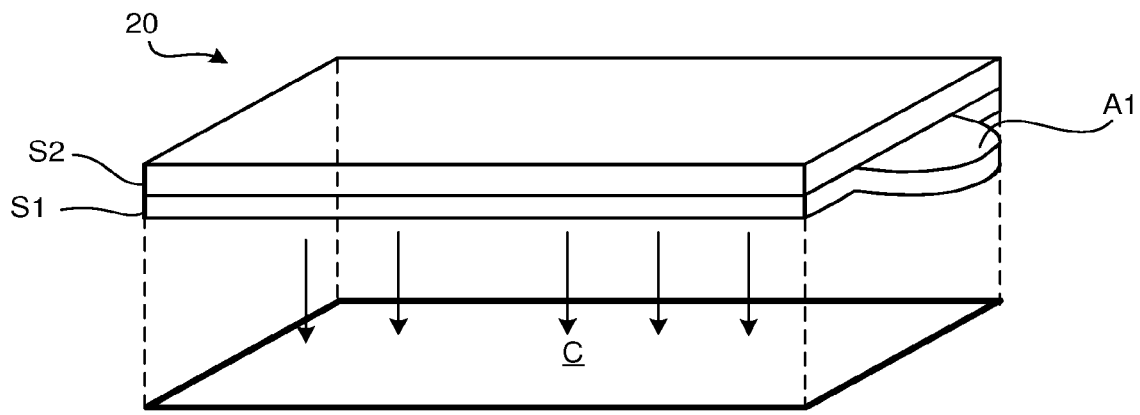
FIGS. 4A and 4B illustrate an example of the embodiment of the amplification chamber that can be used in the device of FIG. 2.
Figure 4B:
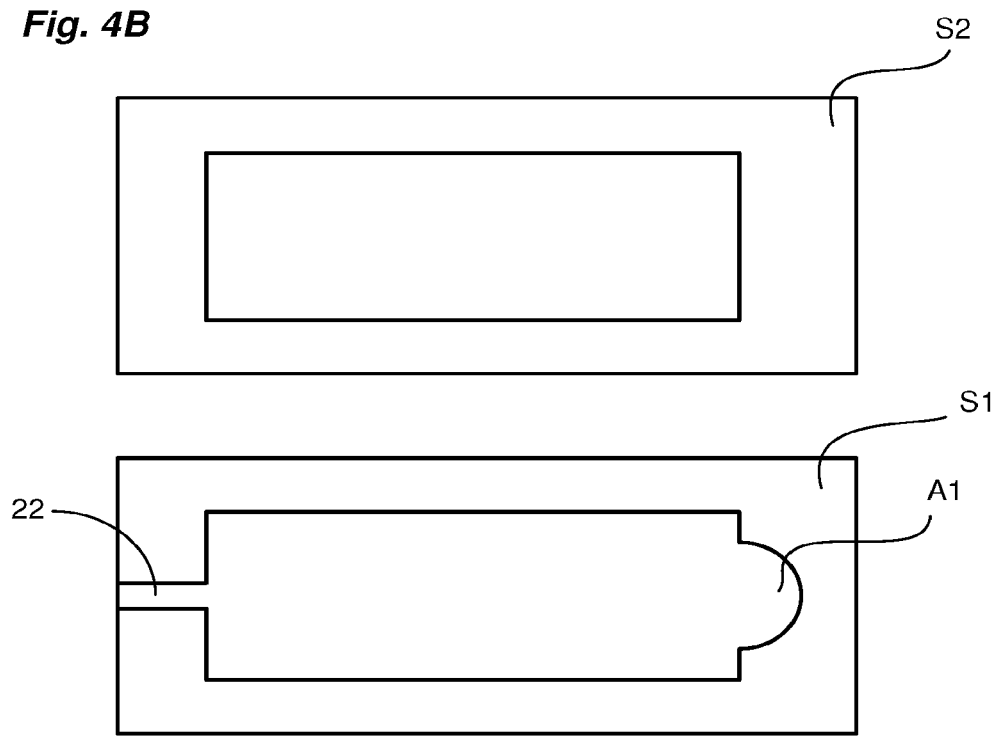

This multilayered principle is illustrated in FIGS. 4A and 4B. These figures show a lower stratum S1 bearing a recess A1 and an upper stratum S2 defining the cross section of the optical reading zone Z (represented here in a non-limiting manner with a rectangular shape). The recess A1 is here in the shape of a half-moon. FIG. 4A shows the amplification chamber in the form of a solid and illustrates the position of the sensor C relative to the chamber, the surface of the sensor C defining the optical reading zone Z of the chamber.

As shown in FIG. 4A, the recess A1 can be located outside the optical reading zone Z of the sensor C. In FIG. 4B, the amplification chamber is created by superimposing the two strata S1, S2. This figure also shows the input channel into the chamber, made in the lower stratum S1 and corresponding to the first transfer channel 22.

Figure 5A:
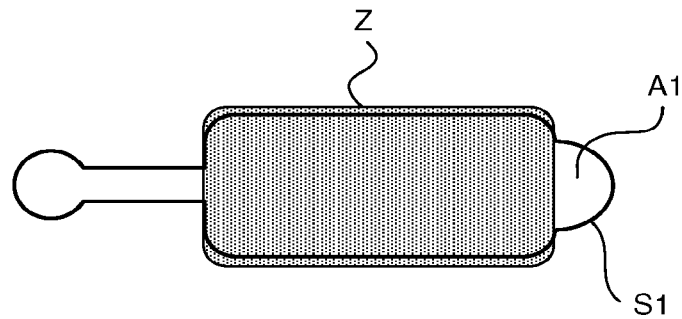
FIGS. 5A to 5C show different alternative embodiments of the amplification chamber embodiment.
Figure 5B:
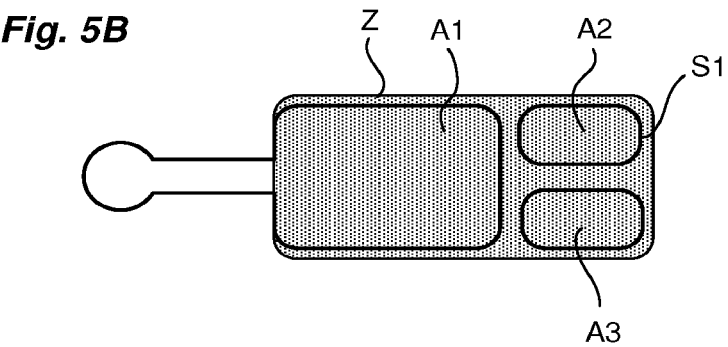
Figure 5C:
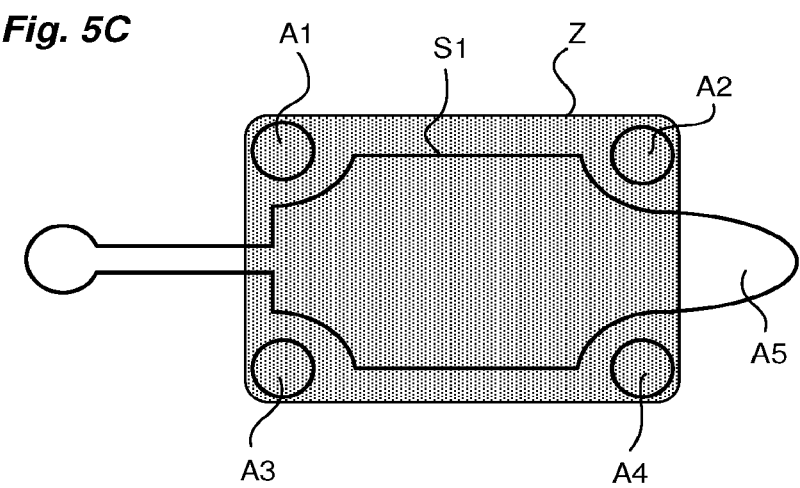

FIGS. 5A to 5C show different architectures of the lower stratum of the amplification chamber. In these figures, the optical reading zone Z is shown in gray.

In FIG. 5A, the lower stratum S1 has a protuberance forming the recess A1 extending beyond the cross section of the optical reading zone Z of the chamber in the transverse plane, opposite the point of liquid entry into the chamber (corresponding to the design of FIGS. 4A and 4B). This offset zone allows the amplification reaction to be shifted temporally and spatially.

In FIG. 5B, the lower stratum S1 has three distinct recesses A1, A2, A3 formed by three cavities to accommodate three distinct primers. These three zones are located in the optical reading zone Z and allow the multiplexing principle to be implemented.

FIG. 5C shows a lower state, defining five distinct zones, four recesses A1-A4 each in the form of a cavity and a main zone comprising a protuberance with a fifth recess A5. The upper stratum of the chamber just above defines the optical reading zone. The optical reading zone Z has a design covering the four recesses A1-A4 so that its volume is in fluid communication therewith. The fifth recess may be outside the optical reading zone Z, as in the design of FIG. 5A.

As described above, each primer can be placed in a separate recess of the chamber in a dry form. To facilitate drying, it is advisable to take the primers in acid buffer (about pH 6) and facilitate their binding with the slide glass. It is also possible to use sugars (for example trehalose) to limit drop diffusion and potentially increase the stability of the dried DNA sequence.

Furthermore, it should be noted that, whatever its architecture, the chamber 20 has rounded angles and contours, allowing for optimal liquid propagation in the chamber and avoiding the formation of bubbles.

From the foregoing it is understood that the device of the invention has many advantages. Its amplification chamber of the device makes it possible to meet several objectives:

Optimize fluidics (absence of bubbles);
Push the air out of the component but retain the liquid;
Not contaminate the environment;
Enable multiplexing;
Host an internal reaction control;
Limit dead volumes; and
Not divide the sample.

The invention claimed is:

1. A microfluidic system intended for the analysis of a biological sample containing biological species, said system comprising:
an optical detection device comprising a source configured to emit an optical signal and at least one sensor having a capture surface defining an optical signal reading zone,
a microfluidic device which comprises:
a support having an amplification chamber configured to carry out an amplification reaction,
an input channel opening into said amplification chamber,
the amplification chamber comprising at least one first zone located in the optical signal reading zone and at least one protuberance forming a recess configured to receive a compound for internal control of the amplification reaction and arranged to be located outside the optical signal reading zone or configured to be opaque to the optical signal.

2. The system according to claim 1, wherein the amplification chamber comprises a first volume having a first section and a second volume having a second section narrowed with respect to the first section so as to form a protuberance, the protuberance forming said recess.

3. The system according to claim 1, wherein the support comprises a plurality of superposed strata and the amplification chamber is formed by at least two of the superposed strata, referred to as an upper stratum and a lower stratum, and the recess is formed in only one of the two strata.

4. The system according to claim 3, wherein the protuberance forming said recess is disposed in the lower stratum.

5. The system according to claim 3, wherein the amplification chamber comprises a main cavity disposed in the upper stratum and one or more secondary cavities disposed in the lower stratum and each forming another recess of the chamber.

6. The system according to claim 1, wherein the recess is configured to receive an internal reaction control compound, comprising a known DNA sequence or a set of DNA primers targeting a predefined DNA target, and configured to allow amplification according to an amplification method used.

7. The system according to claim 1, wherein the first zone of the chamber is transparent for passing an optical signal provided by a source of the detection device and the chamber comprises a second zone having at least one opaque portion configured to not pass the optical signal.

8. A method for analyzing a biological sample containing biological species, said method being implemented by the system according to claim 1, method comprising:
placing an internal reaction control compound in the recess of the amplification chamber,
injecting a fluidic sample into the amplification chamber of the microfluidic device,
detecting with the sensor a presence of a target compound contained in said fluidic sample and located in the first zone of the amplification chamber, and
detecting, with a time lag, a presence of the internal reaction control compound in the first zone of the amplification chamber.

* * * * *